United States Patent
Rau et al.

(10) Patent No.: US 7,104,404 B2
(45) Date of Patent: Sep. 12, 2006

(54) COLLECTING AGENT FOR SULPHIDIC ORES, THE PRODUCTION AND USE THEREOF

(75) Inventors: Tobias Rau, Mainz (DE); Heinrich Hesse, Hattersheim (DE); Wolfgang Buch, Frankfurt am Main (DE); Jaime Gomez, Santiago de Chile (CL); Miguel Angel Arends, Santiago de Chile (CL); Norbert Ernstorfer, Santiago de Chile (CL)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/523,746

(22) PCT Filed: Jul. 22, 2003

(86) PCT No.: PCT/EP03/07966

§ 371 (c)(1),
(2), (4) Date: Feb. 3, 2005

(87) PCT Pub. No.: WO2004/014562

PCT Pub. Date: Feb. 19, 2004

(65) Prior Publication Data

US 2005/0263442 A1    Dec. 1, 2005

(30) Foreign Application Priority Data

Aug. 3, 2002   (DE) ............... 102 35 574
Nov. 12, 2002  (DE) ............... 102 52 451

(51) Int. Cl.
*B03D 1/014*    (2006.01)
*B03D 1/02*     (2006.01)

(52) U.S. Cl. .................................... 209/166; 252/61

(58) Field of Classification Search ............... 209/166, 209/167; 252/61
See application file for complete search history.

(56) References Cited

U.S. PATENT DOCUMENTS

| 1,783,206 A | * | 12/1930 | Wigton ................ 209/166 |
| 1,783,207 A | * | 12/1930 | Wigton ................ 209/166 |
| 1,902,839 A | * | 3/1933 | Cunningham ............... 209/166 |
| 1,974,885 A | * | 9/1934 | Wigton ................ 209/166 |
| 2,134,706 A | * | 11/1938 | Derby et al. ............... 209/166 |
| 2,621,789 A | * | 12/1952 | Booth et al. ............... 209/166 |
| 4,699,711 A | | 10/1987 | Bergmann |
| 4,699,712 A | | 10/1987 | Unger |
| 4,822,483 A | | 4/1989 | Klimpel |
| 2004/0099836 A1 | | 5/2004 | Hesse |

FOREIGN PATENT DOCUMENTS

| DE | 36 29 269 | 3/1988 |
| DE | 4040475 | 7/1991 |
| GB | 2 267 851 | 12/1993 |
| WO | WO 02/38277 | 3/2002 |

OTHER PUBLICATIONS

Florence Klee et al., "Thiophosphoric Acid Derivatives of Ethylamine, dl-Methionine, and I-Proline Ethyl Esters", J. of Pharmaceutical Sci., vol. 51, 1962, pp. 423-427.
Chen Hu, Huaxue Xuebao, (Beilstein Online—Reaction IDS: 183831; 662317; 72722; 68756; 854051), (1956) vol. 22, p. 219.
Ba Khaskin, et al., J. Gen Chem, (Beilstein Online-Reaction IDS: 1165436; 1222107; 1222083; 895279). vol. 43, 1973, p. 1901, USSR.
Heinrich Schubert, "Aufbereitung fester mineralischer Rohstoffe", Band II, 1977, pp. 296-305.
English Abstract of DE 40 40 475, Jul. 4, 1991.

* cited by examiner

*Primary Examiner*—Thomas M. Lithgow
(74) *Attorney, Agent, or Firm*—Richard P. Silverman

(57) ABSTRACT

A method for the flotation of sulfide ores is disclosed. The method comprises contacting the sulfide ores with a composition comprising at least one compound of the formula

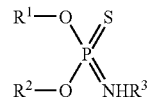

where
$R^1$, $R^2$ and $R^3$ independently of one another are alkyl groups having 1 to 18 carbon atoms, alkenyl groups having 2 to 18 carbon atoms, aryl groups having 6 to 10 carbon atoms, or alkylaryl groups having 7 to 10 carbon atoms.

5 Claims, No Drawings

COLLECTING AGENT FOR SULPHIDIC ORES, THE PRODUCTION AND USE THEREOF

The present invention relates to the use of alkylamidothiophosphoric acid dialkyl esters in the dressing of sulfide ores by flotation, and to a process for preparation thereof.

In the production of sulfide ores and copper/molybdenum ores by flotation, use is made commercially of various collector types, such as dithiophosphates, xanthates, xanthogen formates and thionocarbamates (Schubert: Aufbereitung fester mineralischer Rohstoffe [Dressing of solid mineral raw materials], volume II, 1977, pp. 296 ff.) and mixtures thereof in combination with frothers. The flotation process separates the copper and molybdenum sulfides from gangue minerals.

Collectors cause wetting of the surface of the mineral of value which leads to the particles being rendered hydrophobic. By injecting air into the aqueous flotation pulp, air bubbles are produced, to which the ore particles which have been rendered hydrophobic have a high affinity and are discharged by the air bubbles to the surface of the flotation pulp, while gangue minerals remain in the pulp. Commercially conventional frothers include, for example, alcohols, propylene glycols and also their ethers and MIBC (methyl isobutyl carbinol).

U.S. Pat. No. 4,699,711 discloses a process for the flotation of sulfide minerals using preferably short-chain alkyl-substituted thionocarbamates.

WO 02/38277 discloses the use of mixtures of thionocarbamates and mercaptobenzothiazoles as collectors for the flotation of sulfide ores, in particular copper ore which is associated with molybdenum and gold.

Klee, F. C., Kirch, E. R., J. Pharm. Sci., 51, 1962, 423–427 discloses a process for preparing alkylamidothiophosphoric acid dialkyl esters by reacting $PCl_2SN(C_2H_4)$ with NaOiBu in absolute diethyl ether with the addition of sodium or potassium metal.

It was an object of the present invention to find an improved collector type for sulfidic copper and copper/molybdenum ores which has better flotation results than collectors of the prior art.

It has been found that alkylamidothiophosphoric acid dialkyl esters, in particular ethylamidothiophosphoric acid diisobutyl ester, give a markedly higher recovery for the same copper/molybdenum content. The object of the present invention was in addition to find an improved process for preparing alkylamidothiophosphoric acid dialkyl esters. It should start in particular from more readily accessible starting materials and succeed without absolute solvent and without alkali metals.

The invention thus relates to a composition for the flotation of sulfide ores comprising at least one compound of the formula

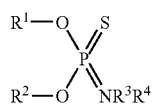

where
$R^1$, $R^2$ and $R^3$ independently of one another are alkyl groups having 1 to 18 carbon atoms, alkenyl groups having 2 to 18 carbon atoms, aryl groups having 6 to 10 carbon atoms, or alkylaryl groups having 7 to 10 carbon atoms, and $R^4$ is hydrogen or alkyl groups having 1 to 18 carbon atoms, alkenyl groups having 2 to 18 carbon atoms, aryl groups having 6 to 10 carbon atoms, or alkylaryl groups having 7 to 10 carbon atoms.

The invention further relates to a process for preparing compounds of the formula

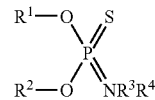

where
$R^1$, $R^2$ and $R^3$ independently of one another are alkyl groups having 1 to 18 carbon atoms, alkenyl groups having 2 to 18 carbon atoms, aryl groups having 6 to 10 carbon atoms, or alkylaryl groups having 7 to 10 carbon atoms, and
$R^4$ is hydrogen or alkyl groups having 1 to 18 carbon atoms, alkenyl groups having 2 to 18 carbon atoms, aryl groups having 6 to 10 carbon atoms, or alkylaryl groups having 7 to 10 carbon atoms, which comprises
a) reacting a dithiophosphate of the formula $(R^1O)(R^2O)PS_2Me$, where Me is a cation, with an oxidizing agent in acidic solution and then
b) reacting the resultant product with an amine of the formula $HNR^3R^4$.

The invention further relates to the use of the inventive flotation reagent for the flotation of sulfide ores. The sulfide ores are preferably copper ores.

The invention further relates to a process for the flotation of sulfide ores by bringing the inventive flotation reagent into contact with the sulfide ores.

With the inventive flotation reagent, improved results for selectivity and yield can be achieved compared with standard collectors in the flotation of nonferrous metal sulfides.

Preferably, $R^1$, $R^2$, $R^3$ and $R^4$ independently of one another are alkyl or alkenyl groups having 1 to 10 carbon atoms. For example, $R^1$, $R^2$ and $R^3$ independently of one another are $C_2$–$C_4$-alkyl groups. Particularly preferably, $R^1$ and $R^2$ are a butyl group, in particular an isobutyl group. $R^3$ is in particular an ethyl group. $R^4$ is in particular hydrogen.

Me is preferably an alkali metal, alkaline earth metal, ammonium ion or hydrogen ion, in particular Na or K.

As oxidizing agent, use can be made of any able to oxidize dithiophosphate, for example a chlorite, for instance sodium chlorite, hypochlorite or chlorate.

As acid, use can be made of any compound which releases hydrogen ions in aqueous solution. Preferably, this relates to mineral acids, for example sulfuric acid, nitric acid, phosphoric acid or hydrochloric acid. If appropriate, the acid can be an oxidizing acid which simultaneously acts as oxidizing agent.

Preferred dithiophosphates are diisobutyl dithiophosphate, diethyl dithiophosphate, diisopropyl dithiophosphate, di-sec-butyl dithiophosphate and diamyl dithiophosphate.

Flotation can be applied to all metal sulfides (apart from Fe), with Cu, Mo, Pb, Zn, and Ni being particularly preferred. Particularly good results are to be observed in the dressing of Cu and Mo. The inventive flotation reagent can be used in a broad pH range (2 to 12) and is added to the aqueous pulp at a concentration between, preferably, 0.001 and 1.0 kg/tonne of crude ore.

The inventive flotation reagent achieves significant improvement of recovery and selectivity compared with the xanthogen formates and thionocarbamates of the prior art.

Examples 1, 3 and 5 clearly show that the recovery of copper and molybdenum is higher than with the corresponding standard reagent. Example 3 is to be emphasized, in which, with 77.3% copper recovery and 69.5% molybdenum recovery, values significantly higher by 4.8 and 7.1% are achieved than with the corresponding amount of ethyl isopropyl thionocarbamate {example 4(V)}, where the copper or molybdenum content remains at the same level.

EXAMPLES

A) Preparation of ethylamidothiophosphoric acid diisobutyl ester:

Stage 1 (Oxidation):

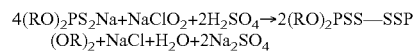

$R=C_4H_9$-isobutyl

Stage 2 Amidation:

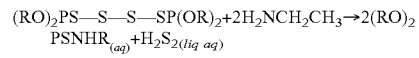  (2a)

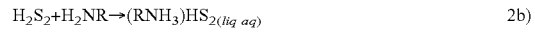  (2b)

To prepare ethylamidothiophosphoric acid diisobutyl ester, 1670 g (3.17 mol) of a 50% strength solution of sodium diisobutyldithiophosphate were homogenized with 725 g of a 22% strength sodium chlorite solution (1.76 mol) for 5 min. 346 g of a 50% strength sulfuric acid were added slowly over 2–3 h with constant stirring, the temperature of the reaction mixture being kept between 40 and 50° C. The mixture was stirred for a further 30 min and the reaction mixture was then cooled to 30–40° C. After separation of the phases, the organic phase (approximately 778 g) was decanted and reacted with 250 g of a 70% strength ethylamine solution which had been added slowly over approximately 2–3 h. The temperature was kept at 40–60° C. by cooling (exothermic reaction). The reaction mixture was then heated under reflux at 70–80° C. for approximately 3 h.

The reaction mixture was cooled to 40–50° C. with stirring, and 441 g of diethylene glycol were added. After a further 30 min, the mixture was cooled to 20–25° C. The concentration of the reaction product was set at the desired active ingredient content using 95 g of water.

After filtration 1551 g of a transparent reddish-oily solution of the product were obtained.

B) Action as Collector

The following collector/frother combinations were used:

TABLE 1

Collector/frother combinations

| Example No. | | Composition |
| --- | --- | --- |
| 1 | Collector: | ethylamidothiophosphoric acid diisobutyl ester (27 g/t) |
|   | Frother: | oxo residue/polypropylene glycol methyl ether, MW = 400 g/mol (5:1, 15 g/t) |
| 2 (control) | Collector: | ethyl isopropyl xanthogen formate (27 g/t) |
|   | Frother: | oxo residue/polypropylene glycol methyl ether, MW = 400 g/mol (5:1, 15 g/t) |
| 3 | Collector: | ethylamidothiophosphoric acid diisobutyl ester (6 g/t) |
|   | Frother: | oxo residue/polypropylene glycol, MW = 425 g/mol (20 g/t) |
| 4 (control) | Collector: | ethyl isopropyl thionocarbamate (6 g/t) |
|   | Frother: | propylene glycol methyl ether, MW = 250 g/mol/MIBC (1:1, 28 g/t) |

TABLE 1-continued

Collector/frother combinations

| Example No. | | Composition |
| --- | --- | --- |
| 5 | Collector: | ethylamidothiophosphoric acid diisobutyl ester (33 g/t) |
|   | Frother: | oxo residue/polypropylene glycol, MW = 425 g/mol (40 g/t) |
| 6 (control) | Collector: | ethyl isopropyl xanthogen formate (33 g/t) |
|   | Frother: | oxo residue/pine oil (6:4, 40 g/t) |

Oxo residues here have roughly the following composition:

| Constituent | Concentration range (% by weight) |
| --- | --- |
| di-2-ethylhexyl ether | 10–25 |
| 2-ethylhexanoic acid 2-ethylhexyl ester | 10–25 |
| $C_{16}$ lactones | 4–20 |
| 2-ethylhexyl butyrate | 3–10 |
| 2-ethylhexane-1,3-diol mono-n-butyrate | 5–15 |
| 2-ethylhexanol | 4–10 |
| $C_4$- to $C_8$-acetals | 2–10 |
| 2-ethylhexane-1,3-diol | 2–5 |
| ethers and esters $\geq C_{20}$ | 0–20 |

TABLE 2

Results of the flotation experiments

| Example No. | Feed | | Concentrate | | | |
| --- | --- | --- | --- | --- | --- | --- |
|   | Cu content in % | Mo content in % | Cu content in % | Mo content in % | Recovery in % | Recovery in % |
| 1 | 1.13 | 0.03 | 11.4 | 0.25 | 92.1 | 80.3 |
| 2 (control) |  |  | 11.5 | 0.23 | 91.2 | 76.9 |
| 3 | 0.62 | 0.017 | 4.1 | 0.14 | 77.3 | 69.5 |
| 4 (control) |  |  | 4.3 | 0.15 | 72.5 | 62.4 |
| 5 | 0.83 | — | 10.3 | — | 89.2 | — |
| 6 (control) |  |  | 10.2 | — | 86.7 | — |

The invention claimed is:

1. A method for flotation of sulfide ores, said method comprising contacting said sulfide ores with at least one compound of the formula

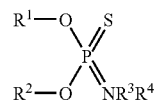

where $R^1$, $R^2$ and $R^3$ independently of one another are alkyl groups having 1 to 18 carbon atoms, alkenyl groups having 2 to 18 carbon atoms, aryl groups having 6 to 10 carbon atoms, or alkylaryl groups having 7 to 10 carbon atoms, and $R^4$ is hydrogen or alkyl groups having 1 to 18 carbon atoms, alkenyl groups having 2 to 18 carbon atoms, aryl groups having 6 to 10 carbon atoms, or alkylaryl groups having 7 to 10 carbon atoms and subjecting the contacted sulfide ore to flotation.

2. The method of claim 1, wherein $R^1$, $R^2$ and $R^3$ independently of one another are $C_2$–$C_4$-alkyl groups.

3. The method of claim 1, wherein said contacting occurs in a pH range from 2 to 12.

4. The method of claim 1, wherein the compound is present in amounts of 0.001 to 1.0 kg per tonne of said ores.

5. The method of claim 1, wherein said sulfide ores are nonferrous sulfide ores, the nonferrous sulfide ores selected from the group consisting of copper sulfide, nickel sulfide, zinc sulfide, lead sulfide, molybdenum sulfide, and mixtures thereof.

* * * * *